United States Patent [19]

Arretz

[11] Patent Number: 4,507,505

[45] Date of Patent: Mar. 26, 1985

[54] PRODUCTION OF 2-MERCAPTO ETHANOL-1

[75] Inventor: Emmanuel Arretz, Pau, France

[73] Assignee: Societe Nationale Elf Aquitaine (Production), France

[21] Appl. No.: 477,358

[22] Filed: Mar. 21, 1983

Related U.S. Application Data

[63] Continuation of Ser. No. 267,552, May 27, 1981, abandoned.

[30] Foreign Application Priority Data

Jun. 6, 1980 [FR] France ............................. 80 12621

[51] Int. Cl.$^3$ ........................................... C07C 149/18
[52] U.S. Cl. ..................................................... 568/62
[58] Field of Search ......................................... 568/62

[56] References Cited

U.S. PATENT DOCUMENTS

| | | | |
|---|---|---|---|
| 3,086,997 | 4/1963 | Warner | 568/62 |
| 3,290,383 | 12/1966 | Pfulgfelder et al. | 568/62 |
| 3,366,693 | 1/1968 | Randall et al. | 568/62 |
| 3,394,192 | 7/1968 | Jones | 568/62 |
| 3,662,004 | 5/1972 | Umbach et al. | 568/62 |
| 3,710,439 | 1/1973 | Goetze et al. | 568/62 |
| 4,281,202 | 7/1981 | Buchholz et al. | 568/62 |

FOREIGN PATENT DOCUMENTS

| | | | |
|---|---|---|---|
| 585655 | 2/1947 | United Kingdom | 568/62 |
| 988135 | 4/1965 | United Kingdom | 568/62 |

OTHER PUBLICATIONS

Malinovskii, Epoxides and Their Derivatives, p. 197, (1965).

*Primary Examiner*—Donald G. Daus
*Assistant Examiner*—S. A. Gibson
*Attorney, Agent, or Firm*—Ostrolenk, Faber Gerb & Soffen

[57] ABSTRACT

Improved process for the production of 2-mercapto ethanol-1 through the action of gaseous hydrogen sulphide on liquid ethylene oxide, under a pressure comprised between 5 and 15 bars and a temperature maintained at between 30° and 70° C., in the presence of a catalyst and/or diluent.

The obtention of mercapto ethanol with excellent yields.

8 Claims, No Drawings

PRODUCTION OF 2-MERCAPTO ETHANOL-1

This is a continuation of application Ser. No. 267,552, filed, May 27, 1981, now abandoned.

The present invention relates to an improvement in the production of 2-mercapto ethanol-1, from ethylene oxide and hydrogen sulphide.

The manufacture of mercapto-ethanol gives rise to somewhat numerous operations, as described in several patents. In general, the yields of the known processes, with respect to ethylene oxide, vary between about 50 and 90%, the latter figure being difficult to reach; if—according to certain patents—said figure could be obtained or even exceeded, it necessitated a high pressure of the H$_2$S used, or otherwise a much longer reaction time. Thus, according to French patent (BASF) publication No. 2 038 977, with reactives in the liquid state, in the presence of thiodiglycol, owing to increased pressures of 25 to 90 atm. a yield of 90% is achieved. According to German Pat. No. 1 221 217 (ROHM and HASS) a yield of 92.4% would be obtained while operating with gaseous reactives, under atmospheric pressure, and extending for several hours the contact between the reacting substances and the thiodiglycol present, and only on condition that the reaction product be substracted, progressively as it forms in order that its content in the medium does not exceed 20%. Without these special steps, if operating occurs with gaseous reactives, even with a high excess of H$_2$S, as described in British Pat. No. 585 655 (WOODWARD) yields do not exceed 64%, unless an ion exchanger resin is used, as prescribed by S.N.P.A. (French patent No. 1 359 678) which enables a yield of 75% to be reached.

This means that, in order to exceed the yield of 90% it is compulsory to apply means which raise the price of and/or complicate the industrial operation in question.

The present invention allows such a situation to be avoided; it makes possible the obtention of mercapto ethanol having excellent yields with respect to ethylene oxide, in conditions of pressure, rate of flow, reaction proportions, temperature, etc. which are perfectly adaptable to an economical industrial exploitation. The process, improved according to the invention, leads to a transformation rate of ethylene oxide of 100%, and a 2-mercapto ethanol-1 selectivity from 95 to 97% with respect to said oxide.

The process according to the invention lies in a very special, unforeseen, combination of different parameters of the reaction of

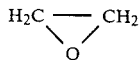

with H$_2$S. It is characterized, in the first place, by the introduction of gaseous hydrogen sulphide into liquid ethylene oxide, whereas the prior technical state always used these two reactives in the same state, gaseous, liquid or dissolved.

Another characteristic, a corollary of the previous one, consists in operating in a strictly determined fairly narrow margin pressure, to wit 5 to 15 bars, and preferably between 8 and 12 bars, whereas the prior art used either atmospheric pressure, or a pressure higher than the 24 bars necessary to maintain both H$_2$S and (CH$_2$)O in the liquid state.

Now, the specific margin of 5 to 15 bars according to the invention is determined by the desired condition of having ethylene oxide in the liquid state, but H$_2$S in the gaseous state, within the temperature limits of the reaction, i.e. between 30° and 70° C. and preferably about 50° to 60° C.

As in all the other known processes, in that of the invention the reactives are in contact with a catalyst and/or diluent, throughout the reaction, Thiodiglycol is especially used, i.e. 2-hydroxy ethyl sulphide, both a known catalyst and diluent, which is furthermore a by-product of the mercapto-ethanol manufacture. The invention may also be carried out in the presence of a catalyst formed by an ion exchange resin, as described in French patent No. 1 359 678 of Société Nationale des Pétroles d'Aquitaine.

Although the HOCH$_2$CH$_2$—S—CH$_2$CH$_2$OH thiodiglycol content in the reaction medium in the production of HS—CH$_2$CH$_2$OH is not critical, it preferably comprises 18 to 40% by weight of this mixture, and most preferably 25 to 32%. Expressed with respect to ethylene oxide, in moles, this thiodiglycol concentration is preferably about 0.2 to 0.4 mole of the latter per (CH$_2$)$_2$O mole, and better still, about 0.3 mole.

It is not worthwhile using a large excess of H$_2$S with respect to (CH$_2$)$_2$O, as is current in certain previous processes; it is advantageous, however, to adjust the H$_2$S inlet in order to have 1 to 1.3 mole H$_2$S and preferably about 1.2 mole, per ethylene oxide mole.

A further advantage of the invention lies in the fact that it enables hydrogen sulphide to be used in the form of certain industrial mixtures, such as for example that of refineries where the gas, known as "acid gas", is accompanied by CO$_2$.

According to the temperature and the pressure selected, the reaction time usually varies between 15 and 120 minutes, but it is preferably from 30 to 60 minutes.

Given the high selectivity of conversion into mercapto-ethanol with respect to ethylene oxide, and the fact that very few by-products form beside thiodiglycol, in the process of the invention, this compound may be recycled such as it is, as a catalyst, without the necessity of a preliminary purification.

Although different apparatus can be adapted to carry out the process of the invention, herein, by way of illustration but without limiting the same, is described a type of apparatus particularly adapted to the present operation. The reactor used is tubular in the form of a column filled with Raschig-rings; it is surrounded by a double jacket, intended to ensure an isothermicity adapted to the reaction medium. The reactor functions cocurrently; in its lower section ethylene oxide and thiodiglycol—both in the liquid state—are injected, while at the same time gaseous hydrogen sulphide is blown in. From the upper part of the reactor, the reaction product is made to flow, continuously, towards the outside. The effluent is thereafter subjected to a distillation in order to separate the 2-mercapto ethanol-1 formed, in a manner known per se.

The contact time of the reaction medium in the reactor, is—of course—the duration of the reaction, which is preferably situated between 30 and 60 minutes.

The example hereafter illustrates, without limiting the same, the present invention.

EXAMPLE

In a tubular reactor of 700 ml serviceable capacity, the reactives are introduced continuously from the bottom.

The hourly flow in moles of the reactives are:
3 for ethylene oxide in the liquid state;
0.82 liquid thiodiglycol;
3.6 gaseous hydrogen sulphide.

There is thus, 11.1 moles catalyst-diluent, thiodiglycol, in 100 moles of the mixture which corresponds to 28.2% by weight. The pressure of the reactor is maintained constantly at 10 bars. The temperature of the reaction medium is adjusted to 50°–55° C. This mixture remains 1 hour in the reactor, i.e. the products, injected at the bottom of the tube, issue transformed at the top of the reactor, one hour later.

It is established that the effluent, gathered in the top of the reactor, is free of ethylene oxide; the conversion rate of that oxide is thus 100%. The effluent issuing comprises 226 g 2-mercapto ethanol-1 which corresponds to a selectivity of 97% with respect to the ethylene oxide, or a yield on this oxide.

The quantity of thiodiglycol formed at the same time does not exceed 6 g, i.e. it remains lower than 3% of ethylene oxide used up.

These results compare advantageously with those of the prior art, in which the maximum yield did not exceed 92.4% (German patent No. 1 221 217—Example 1) whereas the formation of thiodiglycol amounts to 10% of ethylene oxide used (French patent publication No. 2 038 977 page 4 line 4).

This invention is in no way confined to the embodiment described and illustrated here: many variant forms are possible for someone skilled in the art, depending on the applications involved, and without departing from the spirit of the invention.

What is claimed is:

1. An improved process for the production of 2-mercapto ethanol-1 through action of hydrogen sulphide with liquid ethylene oxide, under pressure, in the presence of a catalyst and/or diluent, wherein the hydrogen sulphide in the gaseous state is placed in contact with liquid ethylene oxide, the pressure being adjusted in such a way that the maximum of gaseous $H_2S$ is introduced in the liquid ethylene oxide, in which the temperature of the reaction medium is maintained between 50° and 60° C., the pressure is from 5 to 15 bars, the amount of $H_2S$ is 1 to 1.3 moles per mole of ethylene oxide, the catalyst-diluent is thiodiglycol in an amount of about 0.2 to 0.4 moles per mole of ethylene oxide and the reaction time is from 15 to 120 minutes.

2. A process according to claim 1, in which the temperature of the reaction medium is maintained between 50° and 60° C. and the pressure is from 8 to 12 bars.

3. A process according to claim 2, in which thiodiglycol, formed during the process itself is reused as a catalyst-diluent in a subsequent operation, where the thiodiglycol is used as it remains after the separation of 2-mercapto ethanol-1 produced, without subsequent purification.

4. A process according to claim 2 wherein the hydrogen sulphide is used in the form of an industrial mixture containing $H_2S$.

5. A process according to claim 1, wherein the hydrogen sulphide is used in the form of an industrial mixture containing $H_2S$.

6. A process according to claim 2 wherein the duration of the reaction is from 30 to 60 minutes, the concentration of $H_2S$ is 1.2 moles per mole of ethylene oxide and the concentration of thiodiglycol is about 0.3 moles per mole of ethylene oxide.

7. A process according to claim 6, in which the reaction is carried out continuously through flow in a vertical tubular reactor, wherein the ethylene oxide and the liquid thiodiglycol are injected at the bottom of the reactor simultaneously with a gaseous current of $H_2S$.

8. A process according to claim 1, in which the reaction is carried out continuously through flow in a vertical tubular reactor, wherein the ethylene oxide and the liquid thiodiglycol are injected at the bottom of the reactor simultaneously with a gaseous current of $H_2S$.

* * * * *